United States Patent [19]
Cox et al.

[11] Patent Number: 6,040,452
[45] Date of Patent: Mar. 21, 2000

[54] PROCESS FOR MAKING BENZISOTHIAZOLIN-3-ONES

[75] Inventors: Brian Geoffrey Cox, Huddersfield; Thomas Gray, Haslemere, both of United Kingdom

[73] Assignee: Zeneca Limited, London, United Kingdom

[21] Appl. No.: 09/331,241

[22] PCT Filed: Nov. 13, 1997

[86] PCT No.: PCT/GB97/03130

§ 371 Date: Jun. 18, 1999

§ 102(e) Date: Jun. 18, 1999

[87] PCT Pub. No.: WO98/28283

PCT Pub. Date: Jul. 2, 1998

[30] Foreign Application Priority Data

Dec. 20, 1996 [GB] United Kingdom .................... 9626570

[51] Int. Cl.[7] .................................................. C07D 275/04
[52] U.S. Cl. ............................................................ 548/209
[58] Field of Search ................................................ 548/209

[56] References Cited

U.S. PATENT DOCUMENTS

| | | |
|---|---|---|
| 3,012,039 | 12/1961 | Morley . |
| 4,195,023 | 3/1980 | Mulvey et al. .......................... 548/209 |
| 4,736,040 | 4/1988 | Tonne et al. ............................ 548/209 |

FOREIGN PATENT DOCUMENTS

| | | |
|---|---|---|
| 187 349 | 7/1986 | European Pat. Off. . |
| 94/20479 | 9/1994 | WIPO . |
| 96/29320 | 9/1996 | WIPO . |

*Primary Examiner*—Laura L. Stockton
*Attorney, Agent, or Firm*—Pillsbury Madison & Sutro LLP

[57] ABSTRACT

A process for making a 1,2-benzisothiazolin-3-one by cycling a bisamide precursor under alkaline conditions in the presence of oxygen or an oxygen-release compound in the presence of a nitrogen, sulphur or phosphorus nucelophile. Preferred nucelophiles are ammonia, primary, secondary and tertiary amines, amides, pyridines and quinolines

12 Claims, No Drawings

PROCESS FOR MAKING BENZISOTHIAZOLIN-3-ONES

This application is the national phase of international application PCT/GB97/03130 filed Nov. 13, 1997 which designated the U.S.

This invention relates to a process for making 1,2-Benzisothiazolin-3-ones (hereinafter BIT) by cyclising a bisamide precursor under alkaline conditions using oxygen or an oxygen-release compound in the presence of a nitrogen, suphur or phosphorus nucleophile.

EP 187,349 discloses a process for making BIT by disproportionation and cyclisation of 2,2'-dithiobenzamide under alkaline conditions in the presence of oxygen or an oxygen-release compound.

It has now been found that the reaction rate may be significantly increased by carrying out the disproportionation and cyclisation in the presence of a nitrogen, sulphur or phosphorus nucleophile. In many instances the yield of the BIT is also significantly increased.

According to the invention there is provided a process for making a BIT of formula

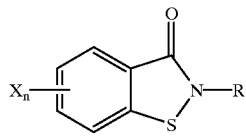

1 wherein
R is hydrogen, aryl, aralkyl, cycloalkyl or $C_{1-20}$-alkyl;
X is halogen, nitro, cyano or $C_{1-6}$-alkoxy; and
n is 0–4;
including salts thereof which comprises reacting a bisamide precursor of formula 2

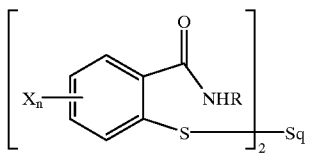

2 wherein
q is 0–3
with oxygen or an oxygen-release compound under alkaline conditions in the presence of a nitrogen, sulphur or phosphorus nucleophile.

When R is aryl it is preferably phenyl.
When R is aralkyl it is preferably benzyl or 2-phenylethyl.
When R is cycloalkyl it preferably contains not greater than 10 and especially not greater than 8 carbon atoms. Examples of cycloalkyl groups are cyclopropyl and cyclohexyl.

When R is $C_{1-20}$-alkyl, it may be linear or branched and is preferably $C_{1-12}$- and especially $C_{1-10}$-alkyl. Examples of these alkyl groups are methyl, ethyl, isopropyl, n-butyl, tert butyl, 2-methylbutyl, 2-ethylbutyl, 2-ethylhexyl, i-amyl, i-hexyl, n-hexyl and n-octyl.

Halogen is bromine, fluorine and especially chorine.
When present, the substituent X is located preferably in the 5- or 6-position of the BIT molecule and especially in the 6-position.

It is preferred, however, that n is zero.

The salts of BIT of formula 1 may be those of an inorganic or organic acid such as acetic, propionic, sulphuric, phosphoric or hydrochloric acid. However, when R is hydrogen, the BIT may also form a salt with a cation such as an ammonium or alkali metal cation. Preferred alkali metal cations are those obtainable from the alkali metal hydroxides. Preferred alkali metals are lithium, potassium and especially sodium.

The bisamide of formula 2 is preferably a 2,2'-dithiobenzamide (q is zero) but may include higher sulphur analogues (q is 1 or more) including mixtures thereof. It is preferred, however, that q is zero.

The process according to the invention has been found especially useful for making 1,2-benzisothiazolin-3-one itself (R is H).

The nitrogen, sulphur or phosphorus nucleophile may be any organic compound (including ammonia) which contains a lone pair of electrons on a nitrogen, sulphur or phosphorus atom and which is substantially inert as far as the bisamide and BIT are concerned. These nitrogen, sulphur and phosphorus nucleophiles include hard, borderline and soft Lewis Acids and Bases as set forth in "Mechanism and Theory in Organic Chemistry" ($3^{rd}$ Edition) by T. H. Lowry and K. S. Schueller, Harper and Row, New York, 1987 on pages 318 to 322, particularly the bases and especially those detailed in Table 3.21.

Preferred nitrogen nucleophiles are ammonia, primary, secondary and particularly tertiary amines, amides, pyridines and quinolines. Preferred amines are those containing $C_{1-12}$-alkyl groups, more preferably $C_{1-8}$-alkyl groups and especially $C_{1-4}$-alkyl groups. Examples of such amines are n-butylamine, 2-ethylbutylamine, 2-ethylhexylamine, trimethylamine and triethylamine. Especially preferred amides are the $C_{1-4}$alkyl amides of $C_{1-4}$-fatty acids such as dimethylformamide and dimethylacetamide. Pyridine nucleophiles include pyridine itself and substituted pyridines, especially those substituted by amino or $C_{1-4}$-substituted amino groups such as 4-dimethylaminopyridine.

Preferred sulphur nucelophiles are organic compounds containing a thione group and especially thioureas. The thiourea may be substituted by phenyl, chlorophenyl, $C_{1-4}$-alkyl or $C_{1-4}$-alkoxy groups. Preferably, the thiourea is unsubstituted.

Preferred phosphorus nucleophiies are those containing three organic groups such as triaryl or trialkyl phosphines. Aryl is preferably phenyl and alkyl is preferably $C_{1-6}$-alkyl. Examples of phosphorus nucleophiles are tri-phenyl and tri-ethyl phosphine.

It is preferred that the MW of the nucleophile is less than 400, more preferably less than 300 and especially less than 200. Particularly useful effects have been obtained with nucleophiles having a MW less than 150 and especially less than 130.

Preferred nucleophiles are ammonia, triethylamine, thiourea and 4-dimethylaminopyridine.

The reaction between the bisamide and oxygen or oxygen-release compound is preferably carried out in a polar liquid. Preferably, the polar liquid is water or more preferably a mixture of water and an organic liquid.

The organic liquid may be polar or substantially non-polar. The term "polar" means an organic liquid capable of forming moderate to strong bonds as described in the article entitled "A Three Dimensional Approach to Solubility" by Crowley et al in Journal of Paint Technology, Vol 38, 1966, at page 269. Such organic media generally have a hydrogen bonding number of 5 or more as defined in the abovementioned article.

Examples of suitable polar organic liquids are amines, ethers, especially lower alkyl ethers, organic acids, esters, ketones, glycols, alcohols and amides. Numerous specific examples of such moderately strongly hydrogen bonding liquids are given in the book entitled "Compatibility and Solubility" by Ibert Mellan (published in 1968 by Noyes Development Corporation) in Table 2.14 on pages 39 to 40 and these liquids all fall within the scope of the term polar organic liquid as used herein.

Preferred polar organic liquids are dialkyl ketones, alkyl esters of alkane carboxylic acids and alkanols, especially such liquids containing up to, and including, a total of 6 carbon atoms. As examples of the preferred and especially preferred liquids there may be mentioned dialkyl and cycloalkyl ketones, such as acetone, methyl ethyl ketone, diethyl ketone, di-isopropyl ketone, methyl isobutyl ketone, di-isobutyl ketone, methyl isoamyl ketone, methyl n-amyl ketone and cyclohexanone; alkyl esters such as methyl acetate, ethyl acetate, isopropyl acetate, butyl acetate, ethyl formate, methy propionate and ethyl butyrate, glycols and glycol esters and ethers, such as ethylene glycol, 2-ethoxyethanol, 3-methoxypropylpropanol, 3-ethoxypropylpropanol, 2-butoxyethyl acetate, 3-methoxypropyl acetate, 3-ethoxypropyl acetate and 2-ethoxyethyl acetate, alkanols such as methanol, ethanol, n-propanol, isopropanol, n-butanol and isobutanol and dialkyl and cyclic ethers such as diethyl ether and tetrahydrofuran.

The substantially non-polar, organic liquids which may be used, either lone or in admixture with the aforementioned polar solvents, are aromatic hydrocarbons, such as toluene and xylene, and halogenated aliphatiz and aromatic hydrocarbons, such as trichloro-ethylene, perchloroethylene and chlorobenzene.

It is preferred that the organic liquid is mono- or dichlorobenzene.

It is especially preferred that the polar liquid is a mixture of water and monochlorobenzene.

The amount of nucleophile varies but is generally less than 5 moles, preferably less than 3 moles and especially less than 1 mole per mole of the bisamide.

When oxygen is used to convert the bisamide to BIT it may be in the form of oxygen gas itself or may be in diluted form such as air. The latter is preferred because of economy and safety in use. Air is also preferred because of its lower reactivity since this reduces the risk of formation of oxidised by-products of thiols during the reaction and consequential reduction in the yield of BIT.

When oxygen (or air) is used, the amount present is preferably in excess of the molar amount of bisamide and is more preferably from 1.0 to 10.0 moles oxygen per mole of bisamide. The oxygen (or air) is preferably introduced either below the surface of the polar liquid or into the vortex created by rapid stirring of the polar liquid during the reaction.

The oxygen-release compound may be organic or inorganic. Examples include hydrogen peroxide itself, organic peroxy acids such as peracetic acid, perbenzoic acid and perphthalic acid. Examples of inorganic oxygen-release compounds are alkali metal perborates and permanganates.

When oxygen-release compounds are used greater care relating to reaction conditions and concentration is required to avoid the formation of oxidised by-products of thiols and the conversion of BIT to saccharins. Preferably shorter reaction times and lower temperatures are required and the oxygen-release compound is preferably added portionwise. It is also preferred that the molar amount of oxygen-release compound is from 1.0 to 5.0, more preferably from 1.0 to 3.0 and especially from 1.0 to 2.0 moles/mole bisamide.

The alkali conditions for the reaction are preferably generated by addition of an alkali metal hydroxide such as lithium, potassium or sodium hydroxide or by addition of ammonium hydroxide. The amount of hydroxide is preferred from 1 to 12 moles, more preferably 2 to 10 and especially from 3 to 8 moles hydroxide per mole of bisamide. The preferred pH of the reaction mix is between 8 and 14.

The reaction of the bisamide with oxygen or oxygen-release compound is very facile in the presence of a nitrogen, sulphur or phosphorus nucleophile and hence high reaction temperatures are unnecessary. Preferably, the reaction temperature is below 120° C. and especially below 100° C. It is also preferred to use temperatures above 50° C. and especially above 70° C.

The BIT may be isolated in its salt-free form by neutralisation of the reaction mix and separation of the BIT by any suitable means known in the art, such as filtration.

Where the reaction is carried out in a mixture of water and organic liquid it is preferable to remove the organic liquid, preferably as an azeotropic mixture with water.

Where the BIT is 1,2-benzisothiazolin-3-one, itself, this may be formulated as an alkali metal salt. In this case, it is preferred to remove the organic liquid and to add sufficient alkali, preferably as the hydroxide of an alkali metal, to give an aqueous solution of the BIT.

The process of the present invention may be back-integrated to include the preparation of the bisamide of formula 2 from dithiobenzoic acid (hereinafter DTBA). In this case the amine used to convert the DTBA to benzamide may serve as nitrogen nucleophile. However, the organic liquid must be selected so that it does not interfere with the conversion of DTBA to bisamide.

According to a further aspect of the invention there is provided a process for preparing a BIT of formula 1 which comprises reacting a thiobenzoic acid of formula 3

3

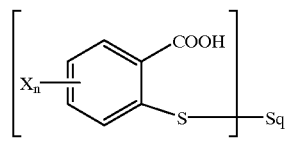

with a chlorinating compound in an inert organic liquid to give a bis-acid chloride and reacting this bis-acid chloride with excess amine of formula $H_2N$-R to form the bisamide of formula 2 which is then converted to BIT by the process as described hereinbefore.

The chlorinating agent is preferably thionyl chloride.

Preferred organic liquids are toluene and especially chlorobenzene.

The reaction between thiobenzoic acid of formula 3 and chlorinating agent is preferably carried out at a temperature between 50 and 80° C. The amount of the amine $H_2N$-R used to react with the bis-acid chloride is not less than 2 moles/mole bis-acid chloride and can be much higher. In the case of volatile amines including ammonia, a large excess may be used to compensate for any losses incurred in the conversion of the bisamide to BIT especially when oxygen or air is used to convert the bisamide to BIT. However, the amount of the amine $H_2N$-R is preferably not greater than 20 moles/mole bis-acid chloride.

The reaction between the bis-acid chloride and the amine $H_2N$-R is preferably carried out at a temperature from 15 to 25° C.

The BIT compounds made by the process according to the invention are biologically active and are useful bactericides and fungicides.

The invention is further illustrated by the following examples wherein references are to parts by weight unless indicated to the contrary.

EXAMPLES 1 to 5

Preparation of BIT from Bisamide 2,2'-dithiobenzamide (79 parts, 0.26M), chlorobenzene (196 parts, 1.74M), water (800 parts) and nucleophilic catalyst were charged to a 1 liter baffled flask equipped with a glass turbine agitator and water condenser to give a cream-coloured suspension. After heating to 55° C., sodium hydroxide (33.2 parts, 0.83M) dissolved in water (66 parts) was added to give a pH of about 10. Air was passed into the vortex of the stirred reaction mix at 55 to 60° C. via an injector positioned approximately 2 cm above the vortex at a rate of 500 ml/min. The reaction was monitored by HPLC and the results recorded in Table 1 below:

TABLE 1

| Example | Catalyst (%) | Moles catalyst/ mole Bisamide | Mole NaOH/ mole Bisamide | Reaction time (mins) | Completion (%) |
|---|---|---|---|---|---|
| 1 | 10% DMAP | 0.1 | 3.15 | 300 | 99.5 |
| 2 | 10% DMAP | 0.1 | 0.55 | 480 | 99.0 |
| 3 | 10% Thiourea | 0.1 | 0.80 | 270 | 99.0 |
| 4 | 300% Et$_3$N | 3.0 | 1.35 | 60 | 99.5 |
| 5 | 100% DMF | 1.0 | 2.52 | 300 | 83.0 |
| Control | — | — | 3.15 | 720 | 30.0 |

Footnote to Table 1
DMAP is 4-dimethylaminopyridine ex. Aldrich
DMF is dimethyformamide ex. Fisons The results in Table 1 show that the presence of a nucleophilic catalyst exhibits a marked increase in the rate of conversion of bisamide compared with the control (EP 187,349).

When Example 1 was repeated where the chlorobenzene was replaced by the same volume of water, the reaction became very frothy and was aborted.

EXAMPLES 6 to 9

Example 1 was repeated using ammonia as the nucleophile and using 2,2'-dithiobenzamide (58.4 parts, 0.19M), chlorobenzene (141 parts, 0.125M), sodium hydroxide (23.9 parts, 0.6M) and water (500 parts) in place of the amounts shown in Example 1. The results are given in Table 2 below and show that ammonia increases the reaction time significantly compared with disproportionation and cyclisation of the bisamide in the presence of aqueous sodium hydroxide alone which is the process of EP 187.349.

TABLE 2

| Example | Catalyst (%) | Moles catalyst/ mol bisamide | Mole NaOH/ mole bisamide | Reaction time (mins) | Completion (%) |
|---|---|---|---|---|---|
| 6 | 15% NH$_3$ | 0.15 | 3.15 | 240 | 99.8 |
| 7 | 300% NH$_3$ | 0.3 | 3.15 | 60 | 99.9 |
| 8 | 300% NH$_3$ | 0.3 | 0 | 90 | 99.8 |
| 9 | 250% NaOH | 0.25 | 2.5 | 420 | 90.4 |

EXAMPLE 10

Integrated preparation of BIT starting from DTBA

Chlorobenzene (220 parts, 1.96M) and dry dimethylformamide (1.43 parts, 0.019M ex. Fisons) were charged to a 1.0 liter jacketed, baffled flask fitted with a glass turbine stirrer and water condenser connected to a caustic scrubber. The apparatus was purged with nitrogen and charged with dithiobenzoic acid (83.2 parts, 0.272M—the dithiobenzoic acid contained 9.6 parts tri-thiobenzoic acid). The flask contents were heated to 70° C. and thionyl chloride (93.8 parts, 0.79M ex. Aldrich) was added dropwise over 30 minutes at 70° C. via a pressure equalising dropping funnel. The reaction was continued for a further 8 hours with stirring at 80° C. During the final 3 hours of the reaction, the flask contents were sparged with nitrogen to remove acid gases and excess thionyl chloride which were detoxified in the caustic scrubber.

Ammonia (94.08 parts, 5.5M) as a 32% (w/w) aqueous solution (ex. Hays Chemicals), water (169 parts) and calsoline oil (6.4 parts ex. ICI) were charged to a 1.0 liter split necked jacketed flask fitted with a glass turbine agitator, jacketed pressure equalling dropping funnel and air inlet tube. The above solution of dithiodibenzoyl chloride in chlorobenzene was added over 30 minutes and the reactants stirred at 20–25° C. for a further 2 hours.

Sodium hydroxide (55 parts, 1.37M) was then added, the reactants heated to 55° C. and air passed into the vortex created by rapid agitation at approximately 2 cm above the surface of the liquors and at a rate of 500 ml/minute. After 60 minutes the reaction was almost complete.

Additional sodium hydroxide (35.4 parts) was added to completely dissolve the BIT and then the monochlorobenzene was removed as an azeotrope at 84–90° C. The volume was maintained by addition of water.

Finally, the reaction mass was cooled to 70° C., acidified to pH6 and cooled further to 25° C. The BIT was then removed by filtration, washed with water and dried to give an off-white solid (124.7 parts, 96.4% theory based on DTBA. Bisamide content, 0.53%).

When the excess ammonia was removed from the bisamide prior to disproportionation/oxidation, the reaction converting bisamide to BIT was only 30% complete after 12 hours.

EXAMPLES 11 AND 12

2,2'-dithio-N-methylbenzamide (44.1 parts, 0.133M), chlorobenzene (98 parts, 0.87M), water (500 parts) and triethylamine (40.4 parts, 0.39M) were charged to a 1.0 liter jacketed baffled flask equipped with glass turbine agitator and water condenser to give a thick, cream-coloured suspension. The reactants were heated to 55° C. and air was introduced via an injector positioned about 2 cm above the vortex of the reaction mixture at a rate of 500 ml/min. The results are given in Table 3 below and show that triethylamine is a more effective catalyst than ammonia for making 2-methyl-BIT. Ammonia as catalyst gives a similar yield and reaction time to the control which is the process disclosed in EP 187,349.

TABLE 3

| Example | Catalyst (%) | Moles catalyst/ mole bisamide | NaOH moles/mole bisamide | Reaction Time (hrs) | Completion (%) |
|---|---|---|---|---|---|
| 11 | 300% Et$_3$N | 3.0 | 0 | 2.5 | 78 |
| 12 | 300% NH$_3$ | 3.0 | 0 | 7.0 | 17.1 |
| Control | — | — | 2.5 | 6.0 | 19.0 |

EXAMPLES 13 AND 14

Example 11 was repeated except using the equivalent moles amount of 2,2'-dithio-N-n-butylbenzamide in place of the methyl analogue. Using 300% triethylamine as catalyst resulted in 40% conversion of the bisamide to 2-n-butyl-BIT in 8 hours irrespective as to whether air or oxygen was used.

We claim:

1. A process for making a 1,2-benzisothiazolin-3-one of formula 1

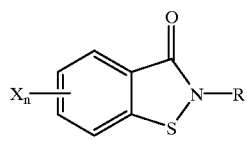
(1)

or salts thereof
wherein
R is hydrogen, aryl, aralkyl, cycloalkyl or $C_{1-20}$-alkyl;
is halogen, nitro, cyano or $C_{1-6}$-alkoxy;
n is 0 to 4;
which comprises reacting a bisamide of formula 2

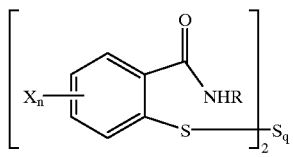
(2)

wherein
q is 0–3
with oxygen or an oxygen-release compound under alkaline conditions in the presence of a nitrogen, sulphur or phosphorus nucleophile substantially inert to 1,2-benzisothiazolinone.

2. A process as claimed in claim 1 wherein n is zero.

3. A process as claimed in either claim 1 or claim 2 wherein q is zero.

4. A process as claimed in either claim 1 or claim 2 wherein the nitrogen nucleophile is selected from ammonia; a primary, secondary or tertiary amine; an amide; a pyridine or substituted pyridine; and a quinoline.

5. A process as claimed in claim 4 wherein the amine is triethylamine.

6. A process as claimed in claim 4 wherein the amide is dimethylformamide.

7. A process as claimed in claim 4 wherein the pyridine is 4-dimethylaminopyridine.

8. A process as claimed in claim 1 or claim 2 wherein the sulphur nucleophile contains a thione group.

9. A process as claimed in claim 8 wherein the sulphur nucleophile is a thiourea.

10. A process as claimed in claim 9 wherein R is H and the 1,2-benzisothiazolinone is in the form of a salt of an ammonia or alkali metal cation.

11. A process as claimed in claim 9 wherein R is methyl or n-butyl.

12. A process for making a 1,2-benzisothiazolin-3-one of Formula 1

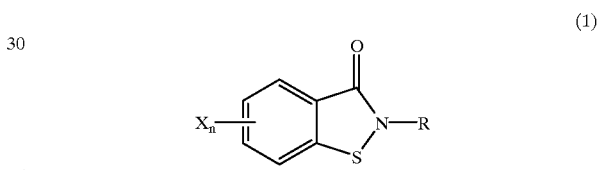
(1)

or salt thereof which comprises reacting a thiobenzoic acid of Formula 3

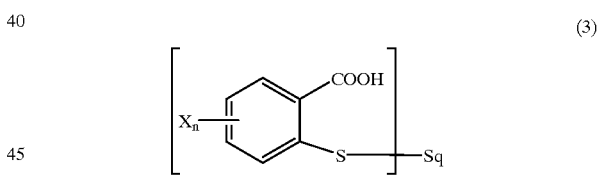
(3)

with a chlorinating compound in an inert organic liquid to give a bis-acid chloride and reacting this bis-acid chloride with excess amine of formula H$_2$N—R to form a bisamide which is converted to a 1,2-benzisothiazolin-3-one by the process as claimed in claim 1, wherein R is hydrogen, aryl, cycloalkyl or $C_{1-20}$-alkyl;
X is halogen, nitro, cyano or $C_{1-6}$alkoxy;
n is 0 to 4; and
q is 0 to 3.

* * * * *